United States Patent [19]

Steinke

[11] 4,224,828
[45] Sep. 30, 1980

[54] NON-SPILL GAS-LIQUID CONTACT UNIT

[75] Inventor: Walter A. Steinke, Edgewood, Md.

[73] Assignee: The United States of America as represented by the Secretary of the Army, Washington, D.C.

[21] Appl. No.: 965,955

[22] Filed: Dec. 4, 1978

[51] Int. Cl.³ .................. B01D 47/02; B01D 53/00
[52] U.S. Cl. .................................. 73/421.5 R; 55/246
[58] Field of Search .................. 55/246, 256, 244; 73/421.5 R

[56] References Cited

U.S. PATENT DOCUMENTS

| | | | |
|---|---|---|---|
| 3,495,440 | 2/1970 | Koblin et al. | 73/28 |
| 3,522,734 | 8/1970 | Curby | 55/256 X |
| 4,099,939 | 7/1978 | Vancheri et al. | 55/246 |
| 4,117,714 | 10/1978 | Goodson et al. | 73/23 |

*Primary Examiner*—Charles A. Ruehl

*Attorney, Agent, or Firm*—Nathan Edelberg; Robert P. Gibson; A. Victor Erkkila

[57] ABSTRACT

A non-spill gas-liquid contact unit for use in a portable detector device for testing the atmosphere for the presence of hazardous substances. The gas-liquid contact unit includes a tubular chamber for absorber liquid, surmounted by a tubular air chamber removably attached thereto by a fluid tight joint, and a breather tube for drawing environmental air through the absorber liquid. The air chamber possesses an axial gas inlet tube projecting from its lower end for admitting gas from the absorber chamber, and an axial gas outlet tube whose one end projects into the upper end of the air chamber and the other end can be connected to a vacuum pump. The air chamber with its inlet and outlet tubes functions as a lock so that, when the unit is accidentally tilted from the normally vertical position to a horizontal or an inverted position while it is under vacuum, the liquid cannot spill out of the unit and thus nullify the analysis and corrode the vacuum pump.

13 Claims, 3 Drawing Figures

NON-SPILL GAS-LIQUID CONTACT UNIT

GOVERNMENTAL INTEREST

The invention described herein may be manufactured, used and licensed by or for the Government for governmental purposes without payment to me of any royalty thereon.

BACKGROUND OF THE INVENTION

Subject invention relates to a novel gas-liquid contact unit, which can be employed in conjunction with a portable detector device for testing the atmospheric environment for the presence of toxic substances. The detector device includes a gas-liquid contact unit, hereinafter referred to briefly as a bubbler unit, connected by tubing to a small, battery powered vacuum pump, and a harness to permit carrying the device by the person. The bubbler unit is small enough to fit into the shirt pocket of the wearer and contains a suitable liquid, eg. an acidic solution, for absorbing one or more toxic or hazardous substances contained in the environmental atmosphere. The pump draws the atmosphere, to which the wearer is exposed, through the bubbler, which monitors the presence and concentration of the hazardous substances in the atmosphere. Thus, the detector device can be worn by the person in hazardous areas, such as chemical plants and laboratories, where it is desired to monitor the presence of one or more toxic substances present in the atmosphere. In operation the vacuum pump draws the atmosphere through the bubbler at a known constant rate. After a suitable period the absorber liquid is removed and analyzed. The concentration of a particular toxic material in the atmosphere breathed by the person can then be calculated from the amount of the toxic material found by analysis in the absorber liquid and the volume of atmosphere introduced.

In the past, a serious deficiency of such portable detector devices has resided in the lack of a satisfactory bubbler unit. In particular, the bubbler unit, when tipped or severely jostled or shaken, allowed the absorber liquid to spill or leak from the unit. Since the bubbler unit is under constant vacuum, the spilled liquid was drawn into the vacuum pump and lost, thereby nullifying the analytical results. Moreover, the vacuum pump would suffer serious damage from the action of the corrosive acidic absorber liquid thus introduced.

SUMMARY OF THE INVENTION

An object of the present invention is to provide a novel bubbler unit which overcomes the disadvantages of bubbler units previously used with portable detectors for testing the atmosphere for the presence of materials of all kinds, including dust, smoke and harmful and toxic substances in the form of gases, vapors or aerosols, particularly when present in abnormal amounts.

Another object is to provide a bubbler unit suitable for use with a portable detector of the aforesaid type, which does not spill or leak when tipped, inverted or shaken.

A further object is to provide a bubbler unit which is rugged in construction and can be readily disassembled to remove the absorber liquid therefrom for analysis.

Other objects will become apparent as the invention is further described.

In accordance with this invention there is provided a bubbler unit comprising an absorber chamber for containing absorber liquid, an air chamber surmounting said absorber chamber and removably joined thereto by a fluid tight joint means, and a conduit—hereinafter referred to as a breather tube—for passing air from the environment through the liquid in the absorber chamber. The air chamber possesses a gas inlet means such as a tube projecting from its lower end to admit gas from the absorber chamber, and a gas outlet means, such as a tube, one end of which projects into the upper end of the chamber and the other end can be connected to a vacuum pump. The air chamber with its inlet and outlet means functions as a lock, which prevents the absorber liquid from spilling from the bubbler unit when the bubbler unit is accidentally tilted from the normally vertical position to a horizontal position or upside down position, while under vacuum.

DESCRIPTION OF THE PREFERRED EMBODIMENTS OF THE INVENTION

Figure 1:
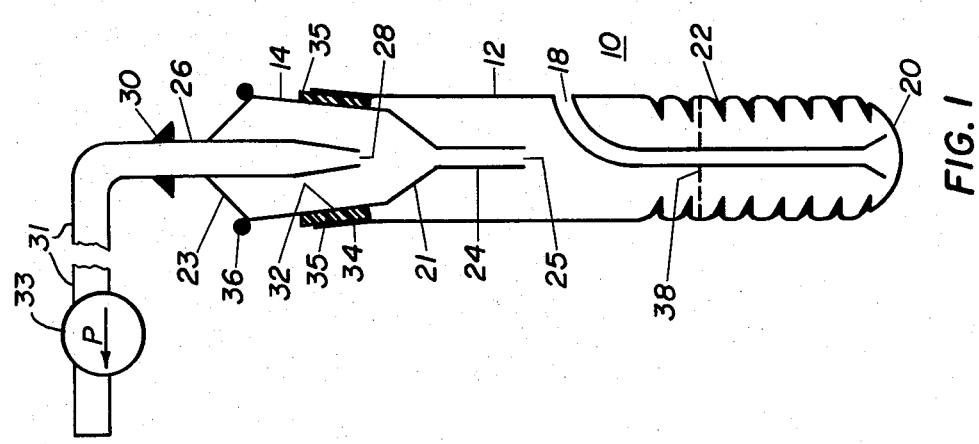
FIG. 1 illustrates a diagrammatic longitudinal cross-sectional view of a preferred embodiment of a bubbler unit of the present invention.

FIG. 1 illustrates a glass bubbler unit 10 consisting of a tubular absorber chamber 12 for containing an absorber liquid (not shown) and an air chamber 14. The absorber chamber 12 contains a breather i.e. gas intake tube 16, which is mounted in and communicates with the environmental atmosphere through sidewall opening 18 and extends nearly to the bottom of the absorber chamber. The breather tube 16 is provided with a flared end 20, which increases the size of the air bubbles produced in the liquid. The wall of the absorber chamber is provided with a series of protuberances 22, which act as baffles to promote agitation of the liquid and promote gas/liquid contact as the bubbles rise through the absorber liquid. The air chamber 14 is of roughly tubular shape with a conical bottom 21 and a conical top 23 and contains a bottom gas inlet tube 24 of small diameter for admitting gas from the absorber chamber 12 and a top gas outlet tube 26 of small diameter connected by a flexible tube or hose 31 to a vacuum pump 33. The gas inlet tube 24 projects into the absorber chamber 12 to a point substantially above the liquid level therein. One end of the outlet tube 26 projects into the air chamber 14 and terminates in a constricted end 28 while the other end 30 is provided with a standard Luer type lock as found on syringes, or other suitable means for connection to a conduit or hose leading to the vacuum pump. The inlet and outlet tubes are centrally located along the longitudinal axes of the air chamber and absorber chamber. The air chamber 14 is circular in cross-section and has an external tapered ground surface 32 intermediate the ends thereof, which mates with the tapered ground surface 34 of the open end of the cylindrical absorber chamber 12 to provide a fluid tight joint. A sleeve 35 of Teflon (polytetrafluoroethylene) or other suitable plastic material can be glued to the tapered surface 32 of the air chamber to produce a joint which can be more readily separated and eliminates the use of stopcock grease which may introduce pollutants into the absorber liquid. Also, the air chamber 14 is provided with an annular projection or nubs 36 located above the ground surface 32. By placing the arms of a tweezers against the sides of the air chamber below the nubs 36 and applying a prying action, the ground glass joint with or without the Teflon sleeve can be readily separated.

A typical portable bubbler unit illustrated and described above is about 130 mm long from the top of the air chamber outlet tube end 30 to the bottom of the absorber chamber 12. The absorber chamber has an overall length of 102 mm, and a length of 85 mm from the bottom thereof to the lower edge of the ground surface 34. Also, the absorber chamber has an ID (internal diameter) of 15 mm and a breather tube of 2 mm ID, one end of which is mounted in sidewall opening approximately midway between the top and bottom of the chamber and the other end terminates about 7 mm from the bottom of the chamber in a flared end of 4 mm diameter. The air chamber 14 from the outlet tube end 30 to the end of inlet tube 24 is 75 mm long. The inlet tube 24 is 20 mm long with and ID of 3.5 mm and terminates at a level approximately 5 mm above the sidewall opening of the breather tube 16. The outlet tube 26 is 37 mm long with an ID of 2 mm, of which 27 mm projects into the air chamber and 10 mm extends out of said chamber.

In operation the absorber chamber 12 is filled with about 3 milliliters of suitable absorber liquid to a level shown by dotted line 38 and then joined to air chamber 14. The outlet tube end 30 is then connected to a hose leading to the vacuum pump. The pump is actuated and draws air into the bubbler unit 10 via breather tube 16 at a constant rate of about 2 cu. ft. per minute. The air bubbles through the absorber liquid, which removes the hazardous material present in the air, and then passes successively through inlet tube 24, air chamber 14 and outlet tube 26 to the vacuum pump. If the bubbler unit 10 is accidentally tilted to a horizontal or an inverted position during operation, the absorber liquid cannot flow out of the unit to the vacuum pump, since the air chamber with its inlet and outlet tubes functions as a liquid arrester or lock. Thus, if the bubbler unit is tilted horizontally and there is sufficient free space above the liquid in the absorber chamber, the liquid cannot reach and enter the open end of inlet tube 24 or breather tube 16; however, if the absorber chamber does not contain sufficient free space so that the liquid enters inlet tube 24 and flows into the air chamber, the capacity of the air chamber is sufficiently large so that the liquid level therein cannot reach the open end 28 of the outlet tube 26. Further, should the bubbler unit be accidentally inverted during operation, the liquid level cannot reach the open end 25 of inlet tube 24 if the volume of the liquid is less than the annular free space in the absorber chamber below the open end 25 of the then inverted inlet tube; however, if the liquid volume is greater so that some of the liquid spills via inlet tube 24 into air chamber 14, the capacity of the annular free space in that chamber below the open end 28 of outlet tube 26 is sufficient so that the liquid level cannot reach the open end 28 of said outlet tube and spill out to the vacuum pump. Also, the constricted end 28 of the outlet tube 26 tends to prevent entrained liquid from being carried out of the air chamber. Thus, the inlet and outlet tubes of the air chamber provide a double lock against the spillage of liquid from the bubbler unit.

The novel bubbler unit described above when charged with conventional acidic absorber liquid is highly efficient even at low air flow rates of 30 cc/min. for quantitatively absorbing toxic agent GB present in very low or very high concentrations in the atmosphere. The absorber chamber can be quickly disconnected from the bubbler unit and the absorber liquid analyzed for GB content. The bubbler unit can be provided with another absorber chamber charged with fresh absorber liquid and reused for detection of GB in the atmosphere.

The air chamber 14, which functions as a liquid arrestor or lock according to the present invention, can contain a gas inlet means and a gas outlet means other than an inlet tube 24 and an outlet tube 26 as shown in FIG. 1. For example, the air chamber conical or concave bottom 21 can have a small gas inlet hole rather than a tube at its apex and have a relatively long tapered configuration so as to provide a sufficiently large annular free space in the absorber chamber 12 below said apex hole wherein absorber liquid can be contained when the unit is inverted. Similarly, the air chamber conical top 23 can be inverted and have a gas inlet hole instead of a tube at its apex and have a relatively long tapered shape with its apex pointed down into the air chamber, thereby similarly providing a substantial annular free space in the air chamber 14 below the cone apex hole when the unit is turned upside down. The resulting air chamber provided an effective liquid arrestor or lock, which prevents spillage of absorber liquid from the bubbler unit in similar manner to that described above.

Figure 2:
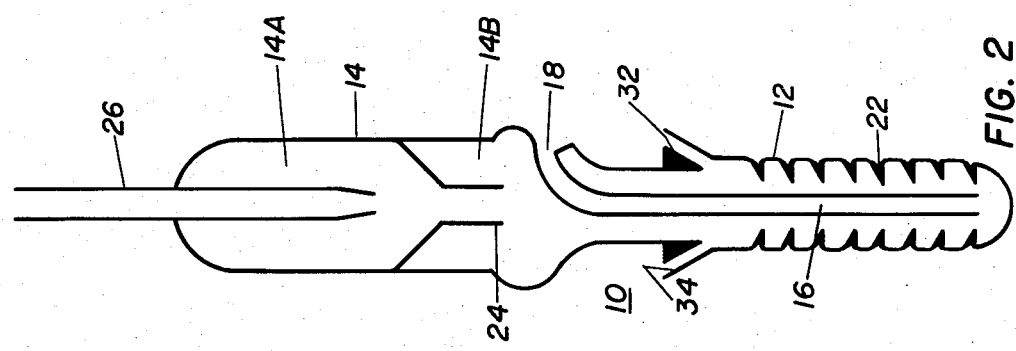
FIG. 2 illustrates a diagrammatic longitudinal cross-sectional view of another embodiment of a bubbler unit of this invention.

FIG. 2 illustrates another embodiment of the nonspill bubbler unit of the present invention. In this embodiment the bubbler unit 10 consists of a tubular absorber chamber 12 and a tubular air chamber 14, which is divided into an upper chamber 14A and a lower chamber 14B. The upper chamber 14A contains a gas inlet tube 24 projecting axially from the bottom thereof into the lower chamber 14B and a gas outlet tube 26, one end projecting axially into the upper chamber 14A and the other end extending from the top of said chamber for connection to a vacuum pump. The lower chamber 14B contains an open end provided with an external ground glass tapered surface 32 which mates with the internal ground glass tapered surface 34 of the absorber chamber 12, and a breather tube 16 which communicates with the atmosphere through sidewall opening 18 and extends nearly to the bottom of the absorber chamber 12 containing projections 22 serving as baffle elements. Thus, chamber 14A with inlet and outlet tubes 24 and 26 functions as the actual liquid arrester or lock, while chamber 14B contains the breather tube 16 mounted in sidewall opening 18 and serves in effect as an extension of the free space above the liquid in the absorber chamber 12.

Figure 3:
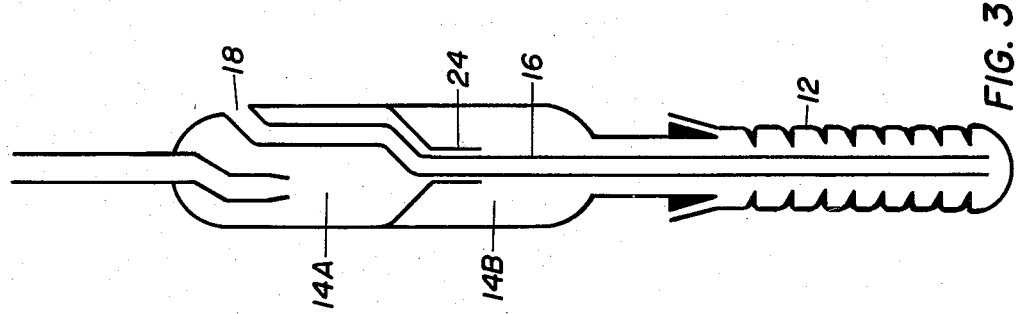
FIG. 3 illustrates a diagrammatic longitudinal cross-sectional view of still another embodiment of a bubbler unit of the present invention.

FIG. 3 illustrates a modification of the bubbler unit shown in FIG. 2, wherein the breather tube 16 communicates with the atmosphere through sidewall opening 18 in the upper chamber 14A, is positioned concentrically in the gas inlet tube 24 and the lower chamber 14B, and extends nearly to the bottom of the absorber chamber 12.

The bubbler unit design shown in FIG. 1 is preferred, since the breather tube is entirely contained within the absorber chamber. This eliminates the possibility of breaking the relatively long and fragile breather tube when it is mounted in the air chamber and extends out of the bottom thereof, as in the units shown in FIGS. 2 and 3. Thus, in the designs shown in FIGS. 2 and 3, the breather tube is relatively susceptible to breakage when the ground glass joint is separated to remove the absorber liquid for analysis, or when it is otherwise accidentally bumped or struck.

The absorber chamber and air chamber are preferably of a generally tubular design but they can also have a nontubular configuration. For example, the air chamber may have a globular shape above its juncture with the absorber chamber. The essential feature of the air chamber is that it functions as a lock at the aforesaid inlet and/or outlet means to prevent spillage or leakage of liquid from the bubbler unit while the bubbler unit is under vacuum. Further, the bubbler unit can be constructed of glass, plastic or other suitable material. Also, the air chamber can be attached to the absorber chamber by any suitable fluid tight means other than a sleeve or ground glass joint, for example, a threaded joint, a sleeve joint or a rubber stopper which fits into the absorber chamber open end and contains a hole for insertion and attachment of the air chamber.

I claim:

1. A non-spill gas-liquid contact unit suitable for use in a portable detector device for testing the atmosphere for the presence of toxic or hazardous substances, comprising in combination:
   an absorber chamber containing a predetermined volume of absorber liquid and having an open end;
   an air chamber surmounting said absorber chamber and having an upper end and a lower end;
   a fluid tight joint means for removably joining said air chamber to said absorber chamber open end;
   a gas intake tube, centrally located in said absorber chamber and connected to a sidewall opening of said absorber chamber or said air chamber, for drawing gas from the environmental atmosphere into said absorber liquid;
   a tube-like inlet means in said air chamber lower end, which projects centrally into said absorber chamber open end, for passage of said gas from said absorber chamber into said air chamber; and
   a tube-like outlet means in said air chamber upper end, which projects centrally into said air chamber, for passage of gas out of said air chamber,
   wherein the capacity of said absorber chamber is sufficiently large so that when the contact unit is tilted horizontally or inverted the absorber liquid level does not reach the open end of said air chamber inlet means or of said gas intake tube, or if exceeded such that liquid spills into said air chamber, the capacity of the air chamber is sufficiently large so that the liquid level does not reach said air chamber outlet means, while said outlet means is connected to a vacuum.

2. A unit according to claim 1, wherein said absorber chamber and said air chamber possess a generally tubular configuration.

3. A unit according to claim 1 or 2, wherein and said outlet means comprises a tube projecting into said air chamber upper end.

4. A unit according to claim 3, wherein said inlet means comprises a tube projecting from said air chamber lower end.

5. A unit according to claim 3, wherein the outlet tube end of said air chamber is constricted.

6. A unit according to claim 1, wherein said gas intake tube is mounted in a sidewall opening of said absorber chamber and entirely contained therein.

7. A unit according to claim 1, wherein said gas intake tube is mounted in a sidewall opening of said air chamber.

8. A unit according to claim 1, wherein said fluid tight joint means comprises a ground glass joint.

9. A unit according to claim 8 wherein the ground glass joint contains a polytetrafluoroethylene sleeve.

10. A unit according to claim 2, wherein said air chamber is joined intermediate the upper and lower ends thereof to said absorber chamber open end.

11. A unit according to claim 2, wherein said air chamber contains at least one external protuberance above said joint means to assist separation of said chamber from said absorber chamber.

12. The combination of a non-spill gas-liquid contact unit according to claim 1 with a vacuum pump.

13. In a gas-liquid contact unit comprising:
   a lower chamber for absorber liquid having an open end;
   an upper chamber having a tube-like inlet means projecting centrally into said lower chamber for passage of gas from said lower chamber into said upper chamber and a tube-like outlet means projecting centrally inwardly into said upper chamber for passage of gas out of said upper chamber;
   a fluid tight joint means for removably joining said lower chamber to said upper chamber; and
   a gas intake tube centrally extending into said lower chamber for absorber liquid,
   the improvement wherein said gas intake tube is mounted in a sidewall opening of said lower chamber and entirely contained therein.

* * * * *